US010817737B2

(12) United States Patent
Kaur

(10) Patent No.: US 10,817,737 B2
(45) Date of Patent: Oct. 27, 2020

(54) SYSTEM AND METHOD FOR SENSING PHYSIOLOGICAL CHARACTERISTICS

(71) Applicant: United States of America, as represented by the Secretary of the Army, Fort Belvoir, VA (US)

(72) Inventor: Balvinder Kaur, Centreville, VA (US)

(73) Assignee: UNITED STATES OF AMERICA, AS REPRESENTED BY THE SECRETARY OF THE ARMY, Washington, DC (US)

( * ) Notice: Subject to any disclaimer, the term of this patent is extended or adjusted under 35 U.S.C. 154(b) by 118 days.

(21) Appl. No.: 16/264,728

(22) Filed: Feb. 1, 2019

(65) Prior Publication Data

US 2020/0250447 A1    Aug. 6, 2020

(51) Int. Cl.
| | |
|---|---|
| G06K 9/40 | (2006.01) |
| G06K 9/42 | (2006.01) |
| G06K 9/00 | (2006.01) |
| A61B 5/0205 | (2006.01) |
| A61B 5/16 | (2006.01) |
| A61B 5/117 | (2016.01) |
| A61B 5/024 | (2006.01) |
| A61B 5/021 | (2006.01) |
| A61B 5/00 | (2006.01) |

(52) U.S. Cl.
CPC ........ *G06K 9/00885* (2013.01); *A61B 5/0205* (2013.01); *A61B 5/117* (2013.01); *A61B 5/165* (2013.01); *G06K 9/40* (2013.01); *G06K 9/42* (2013.01); *A61B 5/0077* (2013.01); *A61B 5/02125* (2013.01); *A61B 5/02405* (2013.01); *A61B 5/02427* (2013.01); *G06K 2009/00939* (2013.01)

(58) Field of Classification Search
None
See application file for complete search history.

(56) References Cited

U.S. PATENT DOCUMENTS

| | | | | |
|---|---|---|---|---|
| 2013/0343614 A1* | 12/2013 | Kyal | ...................... | A61B 5/024 382/107 |
| 2014/0012142 A1* | 1/2014 | Mestha | .............. | A61B 5/02427 600/480 |
| 2017/0354334 A1* | 12/2017 | Tarassenko | ............ | A61B 5/725 |
| 2019/0307365 A1* | 10/2019 | Addison | ................ | A61B 5/743 |
| 2020/0121262 A1* | 4/2020 | De Haan | .............. | A61B 5/0245 |

OTHER PUBLICATIONS

Balvinder Kaur, J. Andrew Hutchinson, Vasiliki N. Ikonomidou, "Visible spectrum-based non-contact HRV and dPTT for stress detection," Proc. SPIE 10221, Mobile Multimedia/Image Processing, Security, and Applications 2017, 102210E (May 10, 2017); doi: 10.1117/12.2261085.

* cited by examiner

*Primary Examiner* — Idowu O Osifade
(74) *Attorney, Agent, or Firm* — Richard J. Kim

(57) ABSTRACT

A sensor system is disclosed, which includes a sensor configured to measure electromagnetic energy levels received from skin of a human subject not in contact with the sensor; a data processing unit configured to determine multiple heart rate metrics of the human subject from the electromagnetic energy levels measured by the sensor; and an output device. The output device is configured to indicate a physiological characteristic of the human subject determined from the multiple heart rate metrics of the human subject determined by the data processing unit.

15 Claims, 11 Drawing Sheets

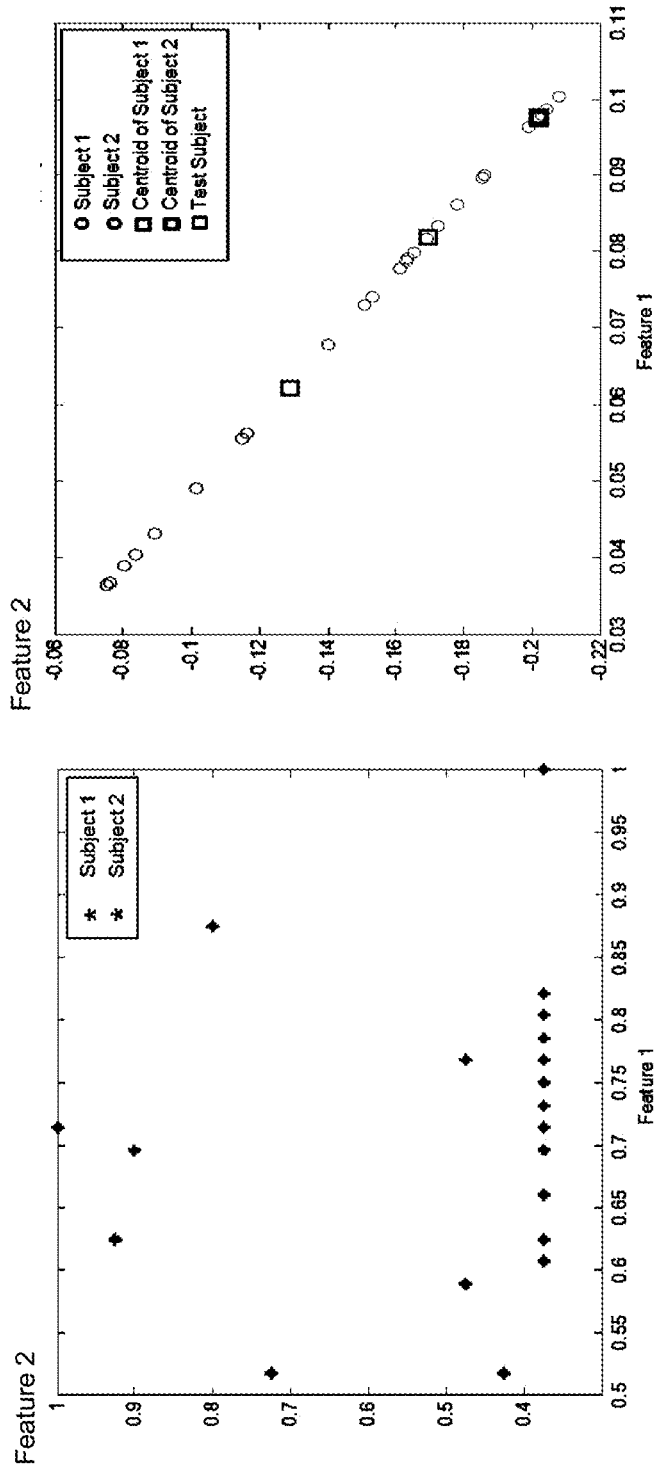

SYSTEM AND METHOD FOR SENSING PHYSIOLOGICAL CHARACTERISTICS

GOVERNMENT INTEREST

The invention described herein may be manufactured, used, sold, imported, and/or licensed by or for the Government of the United States of America.

FIELD OF THE INVENTION

The present subject matter relates generally to sensors, especially non-contact sensors which detect biometric data.

BACKGROUND OF THE INVENTION

Conventional biometric sensors such as electrocardiograph machines require contact with the skin to detect data such as heart rate. This prevents the use of the detector for sensing data from a crowd of people or covert detection. Thus, a non-contact biometric sensor is desired.

SUMMARY OF THE INVENTION

The present invention broadly comprises a sensor system and a method for detecting biometric data.

In one embodiment, the sensor system includes a sensor, a data processing unit, and an output device. The sensor is configured to measure electromagnetic energy levels received from a human subject. The data processing unit is configured to determine heart rate metrics from the electromagnetic energy levels measured by the sensor. The output device is configured to indicate a physiological characteristic of the human subject determined from the heart rate metrics determined by the data processing unit.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which:

FIG. 11a shows an example of two clusters made of feature 1 and feature 2, representing data spread between subject 1 and subject 2 in a normal domain using two features; and FIG. 11b shows an example of two clusters made of feature 1 and feature 2, representing data spread between subject 1 and subject 2 in a least discriminant analysis (LDA) domain.

DETAILED DESCRIPTION

Reference is presently made in detail to exemplary embodiments of the present subject matter, one or more examples of which are illustrated in or represented by the drawings. Each example is provided by way of explanation of the present subject matter, not limitation of the present subject matter. In fact, it will be apparent to those skilled in the art that various modifications and variations can be made in the present subject matter without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the disclosure and equivalents thereof.

Figure 1:
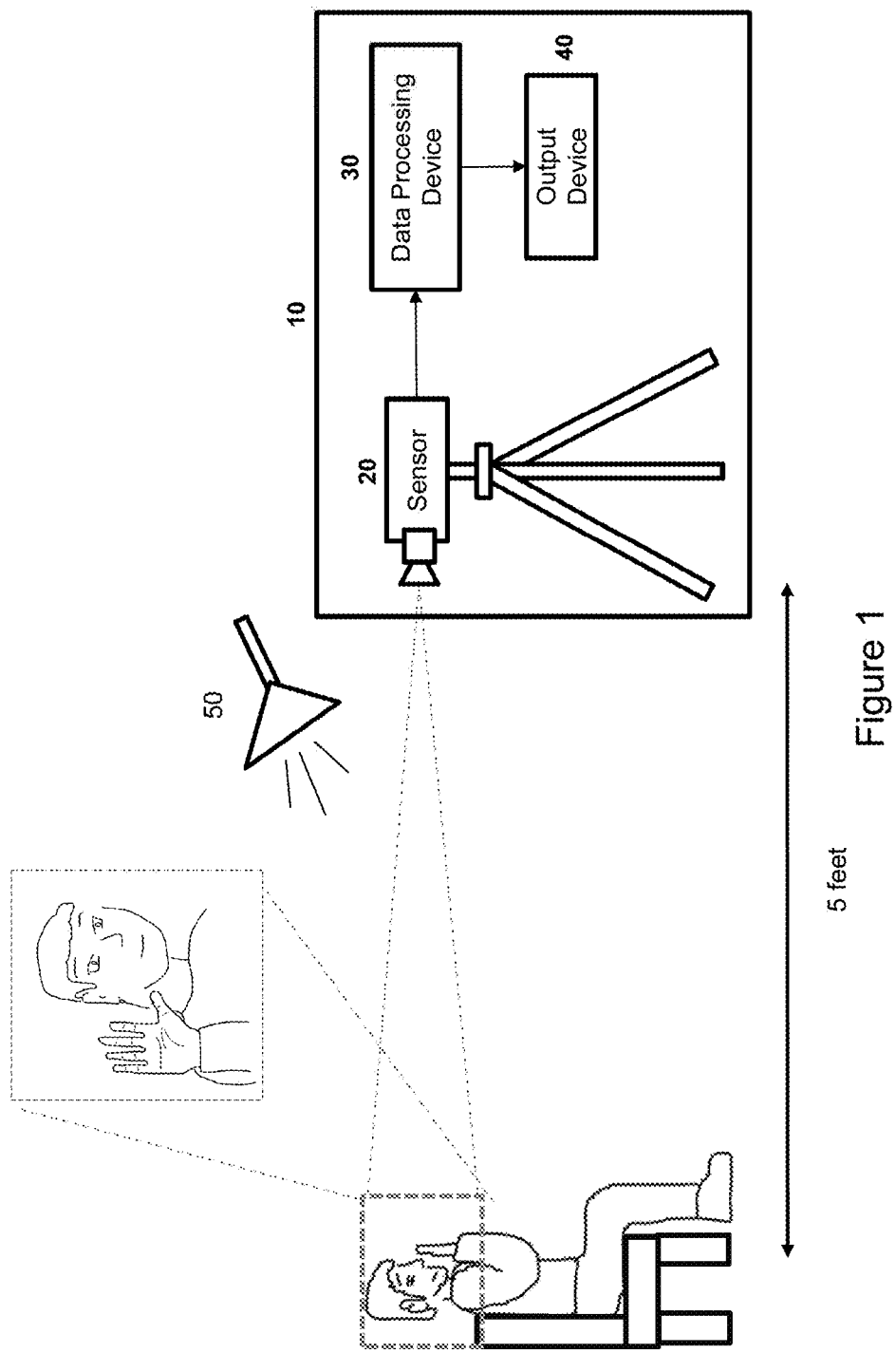
FIG. 1 illustrates one mode of operation, which was used to capture videos, e.g., both facial and palm skin videos simultaneously from a subject sitting in a chair, in a relatively motionless conditions, and facing the sensor.

FIG. 1 illustrates one mode of video operation, e.g., to capture facial and palm skin video clips in a non-contact manner for 30 seconds from a subject, sitting in a chair, facing the sensor, 5 feet away from the subject, under a daylight lamp 50 (e.g., a compact fluorescent lamp), which has broad spectrum with peak in the green band (~535 nm) to approximate sunlight.

Figure 2:
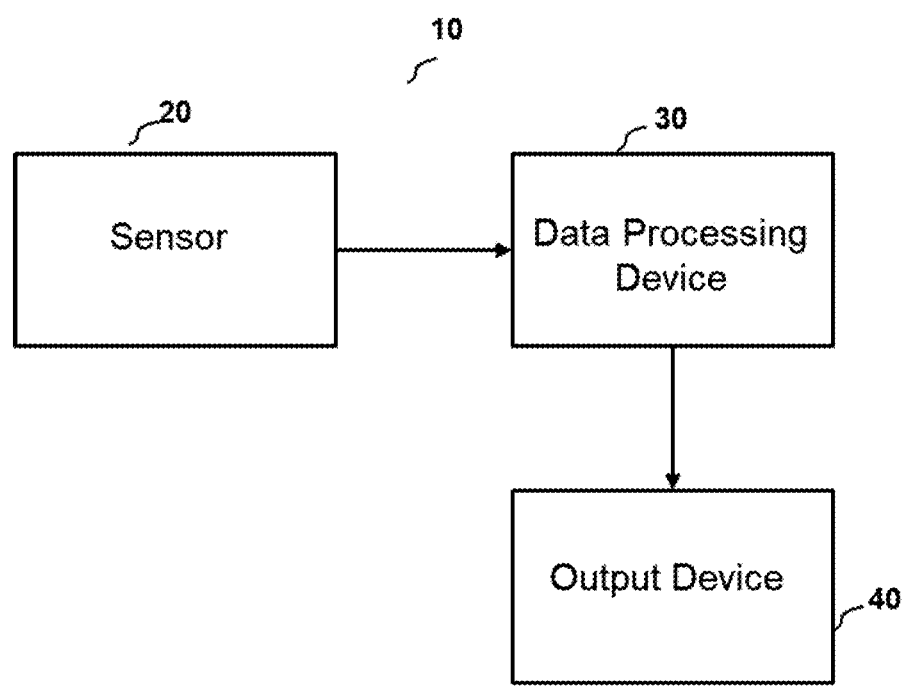
FIG. 2 illustrates a detection device 10 according to a first embodiment of the present invention.

FIG. 2 illustrates the detection device 10 according to a first embodiment of the present invention. Detection device 10 includes a sensor 20, a data processing device 30, and an output device 40. In best mode, we used a Basler scA640-70 gc visible 12-bit video camera as the sensor 20, data processing device 30 is a personal computer, and output device 40 is the display screen of the personal computer. Alternatively, device 10 can be a cellular telephone (cellphone), wherein sensor 20 is the photographic system of the cellphone, data processing device 30 is the cellphone processing device programmed, and output device 40 is the display screen of the cellphone. Both of these embodiments, as well as other configurations and modifications discussed herein, are within the scope of the invention as claimed.

Figure 8:
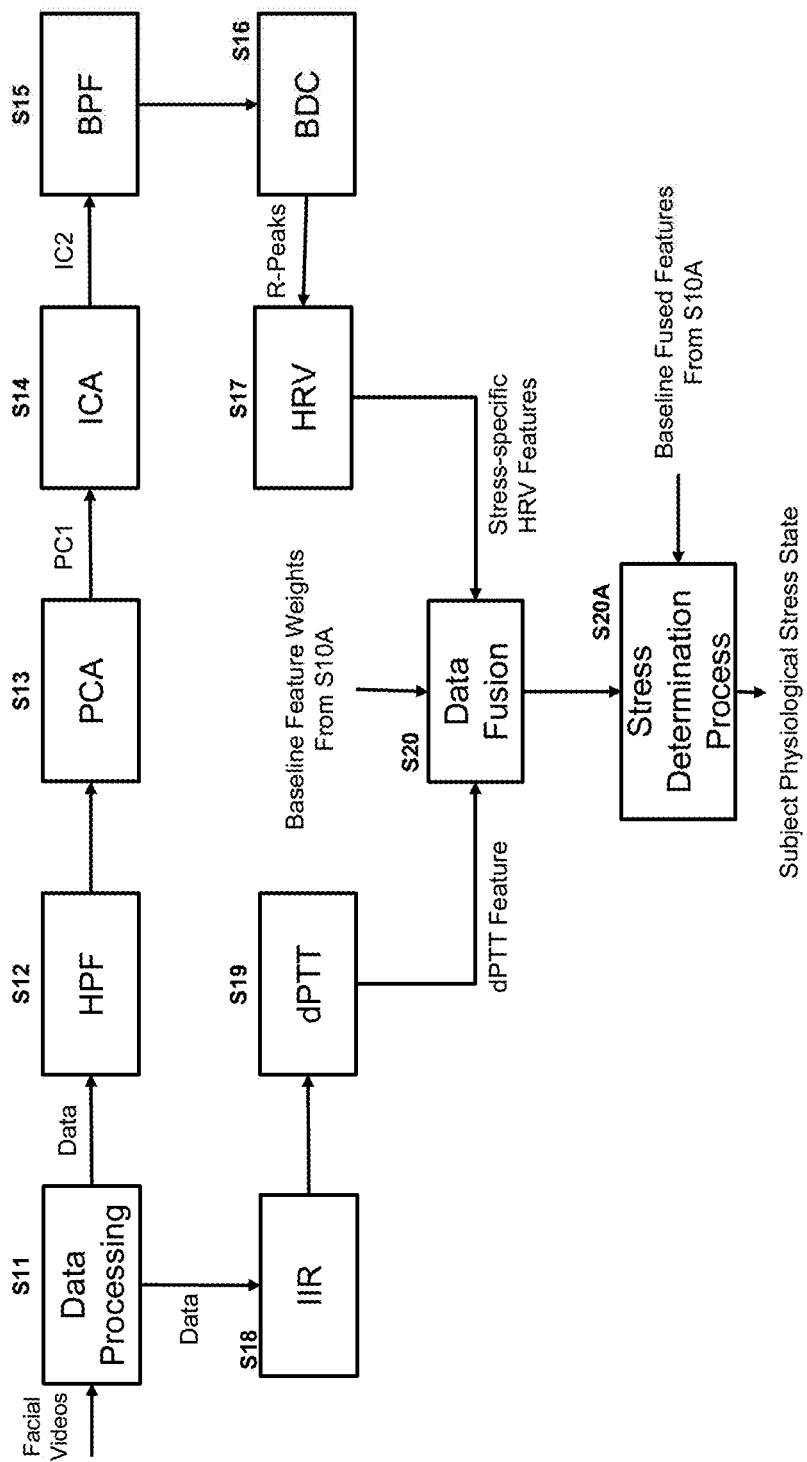
FIG. 8 shows a stress detection data processing algorithm according to the present invention.
Figure 9:
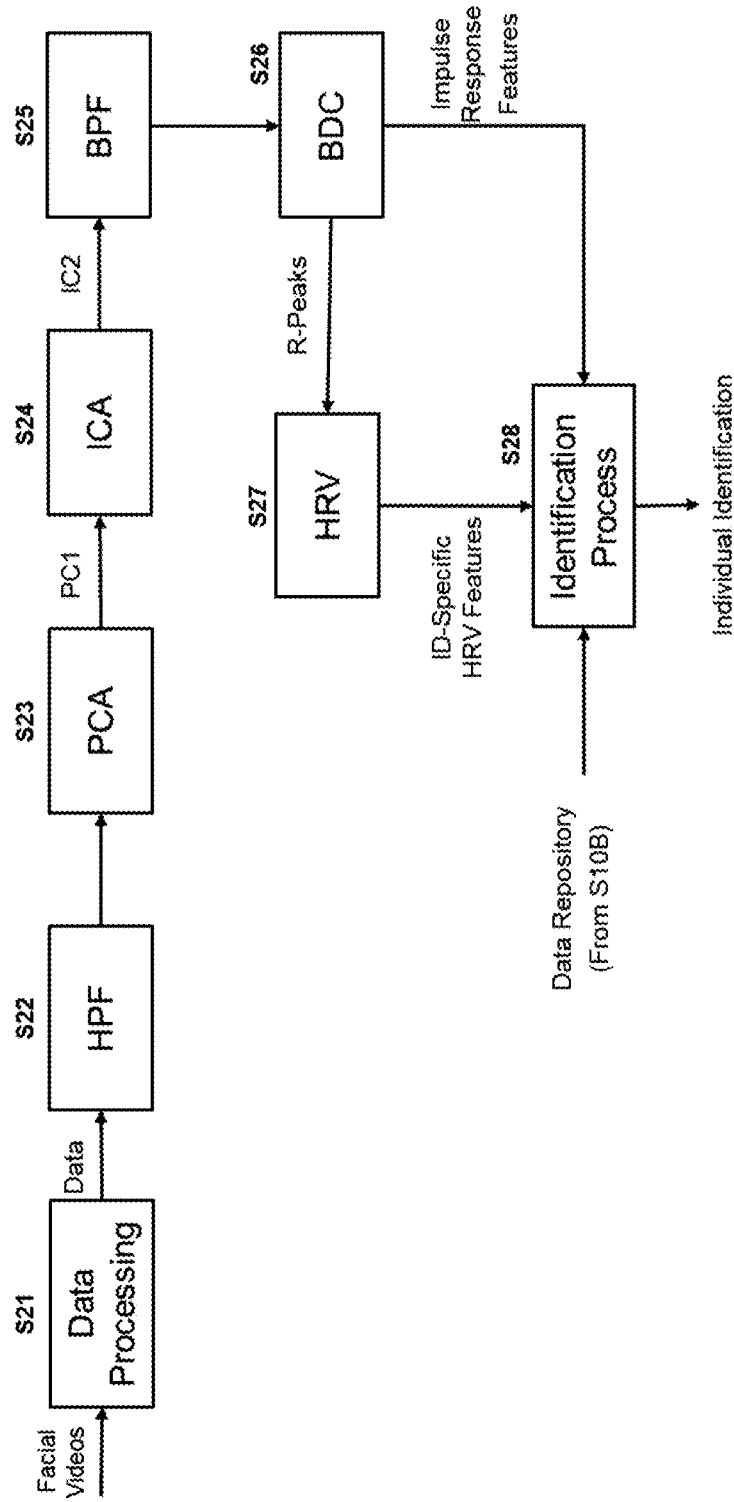
FIG. 9 shows a processing algorithm for an identification device embodiment of the present invention.

Further, detection device 10 is configured in one embodiment to determine a subject's stress level, and, in another embodiment, it is configured to identify the subject. The processing steps for the first embodiment, stress testing, are shown in FIG. 8. The processing steps for the second embodiment, subject identification, are shown in FIG. 9. Both of these embodiments are within the scope of the invention as claimed.

Sensor 20 detects electromagnetic energy reflected by a human skin, higher order statistics of which are used to determine current characteristics of the person observed. In particular, heart pulse signals can be passively obtained from visible spectrum-based video (that is, in a non-contact configuration, in contrast to an electrocardiogram (ECG)). This is possible due to changes in skin reflectivity during the cardiac cycle. As the cardiac systole blood pressure wave front arrives at the skin capillaries, a temporal peak in blood concentration is observed. Oxy- and deoxyhemoglobin, two main blood components that together with melanin influence light absorption at the skin, show significant absorption peaks in the Soret (~400 nm to ~450 nm, corresponding to violet) and q-bands (~500 nm to 600 nm, spanning over green and yellow). As the blood concentration varies over the cardiac cycle, reflectivity changes primarily as intensity fluctuations in the green band of the red, green, and blue (RGB) signal. This data is used to compute two metrics, heart rate variability (HRV) and differential pulse travel time (dPTT).

Thus, as described, sensor 20 is a visible light, detector. However, other detectors, such as thermal and sonic detectors are used as sensor 20, as well as electromagnetic radiation detectors covering the span of 400-2200 nm, and these modifications are within the scope of the invention as claimed.

HRV analysis is based on the measurement of the interval between subsequent heartbeats, which is referred to herein as the RR-interval. dPTT is a non-contact measurable characteristic that correlates with blood pressure. dPTT is the time difference between pulse arrival times at two different distal locations in the body. In one embodiment, dPTT is measured from the imaged forehead and palm Regions of Interest (ROIs) of a subject's pixel images. However, different locations may be used in accordance with the present invention. Thus, embodiments of the present invention measure the RR-interval and dPTT in a non-contact manner, which are then used to determine physiological characteristics of the human subject, such as the stress level of the human subject observed, or the identity of the human subject observed.

Figure 3:
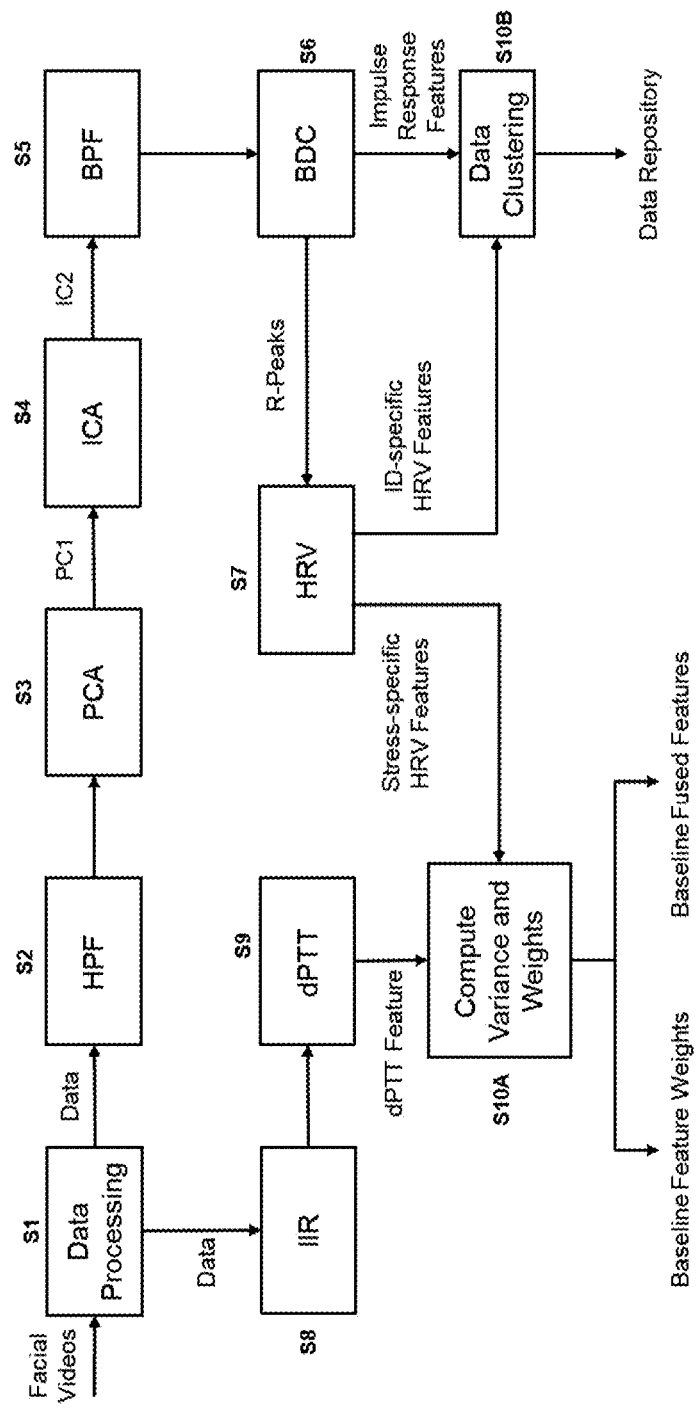
FIG. 3 shows a baseline and repository acquisition data processing algorithm according to a stress detection device embodiment of the present invention.

To accomplish this, FIGS. 3, 8 and 9 indicate facial videos from sensor 20 which images visible light reflected from a facial view to capture two portions of a human subject, such as the palm and the forehead of the subject. In one example, 30 seconds of visible video data is collected by sensor 20. The data received by sensor 20 is sent to data processing device 30.

To detect stress in a subject or to score a subject for best match, first a baseline and repository acquisition process is performed, which is shown in FIG. 3. The input to the process is a facial video from an individual (under his/her normal physiological state) captured with a visible spectrum-based camera and the output of the process is a set of baseline feature weights for a data fusion equation, baseline fused features (dPTT and HRVs), and data repository for identifying subjects. Facial and palm skin video clips of 30 seconds are captured over multiple collections and processed, to compute baseline fused features and baseline feature weights for stress determination (FIG. 8) and data repositories for identifying subjects (FIG. 9). In this regard, output device 40 has a basic or detailed indicator of the baseline and repository acquisition process as described hereafter.

In Step S1, data processing device 30 defines two ROIs of pixels within the video. In one example (FIG. 7a), one ROI is an 11×11 pixel square area on the forehead and the other ROI is an 11×11 pixel square area on the palm. In this example, data processing device 30 constructs an 11×11×N matrix for each ROI (where N=number of frames). Within each ROI, 121 signals are generated from Red, Green, and Blue bands, or the RGB bands. The signals from forehead are processed using steps S1-S7 and HRV features are generated. The signals from Green band (acquired from both palm and forehead) are spatially averaged and processed using steps S8-S9, and dPTT feature is computed. Details of steps S1-S9 are discussed in the subsequent sections.

In Step S2, data processing device 30 removes baseline variations by applying a highpass filter to the raw individual pixel signals from the red, green, and blue bands. The highpass filter has a finite impulse response filter of order 250 and a frequency cutoff of 0.8 Hz. The filtered signals are then used as inputs to the Principal Component Analysis (PCA) algorithm, with the analysis running independently for each color channel.

In Step S3, data processing device 30 denoises (removes phase shift) RGB signal using PCA. One embodiment of an exemplary PCA algorithm is as follows. Data processing device 30 creates a matrix X with the columns representing signal recordings from each repeated collection of data. X can then be considered to have the form $X=USV^T$, where the columns of U contain the eigenvectors of $XX^T$, S is the diagonal matrix, and the rows of $V^T$ are the contributions of each eigenvector to each instance of the signal under examination. The present inventor discovered that the maximum variability in the data resides in the first eigenvector, and therefore this eigenvector is used to determine the PCA components with the best signal in the first component from RGB bands (noted hereinafter as $\overrightarrow{PC1_R}, \overrightarrow{PC1_G}, \overrightarrow{PC1_B}$). The present inventor further noted a heart-beat-like periodicity in the PC1 component in all three bands.

In Step S4, data processing device 30 selects a source from the PC1 component of the RGB data by applying an Independent Component Analysis (ICA) algorithm. The ICA algorithm is based on two principles: 1) Nonlinear decorrelation (whitening) and 2) maximum nongaussianity (rotation of whitened data). The ICA algorithm is applied to the PC1 components and the source signals (columns of S) are computed.

Basic equations to compute the source signals are listed below:

$$X=AS$$

Where, columns of matrix X are the PC1 components of the RGB data after applying the mixing matrix A to the matrix S.

The first step of the ICA algorithm is to compute estimated sources ($\hat{S}$) by first finding the demixing matrix W that is proportional to the inverse of the mixing matrix A.

$$\hat{S}=WX$$

The whitening operation is performed on the input data X to remove any correlation between the signals. During this process, any correlation between the data is reduced to zero and similar variance for each data set. This operation generates the orthogonal basis for the reduced dimensionality components. To confirm the accuracy of the whitening operation, the computed covariance matrix of the whitened data is tested and continued if it is diagonal. Since W is approximately inversely proportional to the matrix A, it is used to rotate the whitened data to generate expected independent components.

Figure 6:
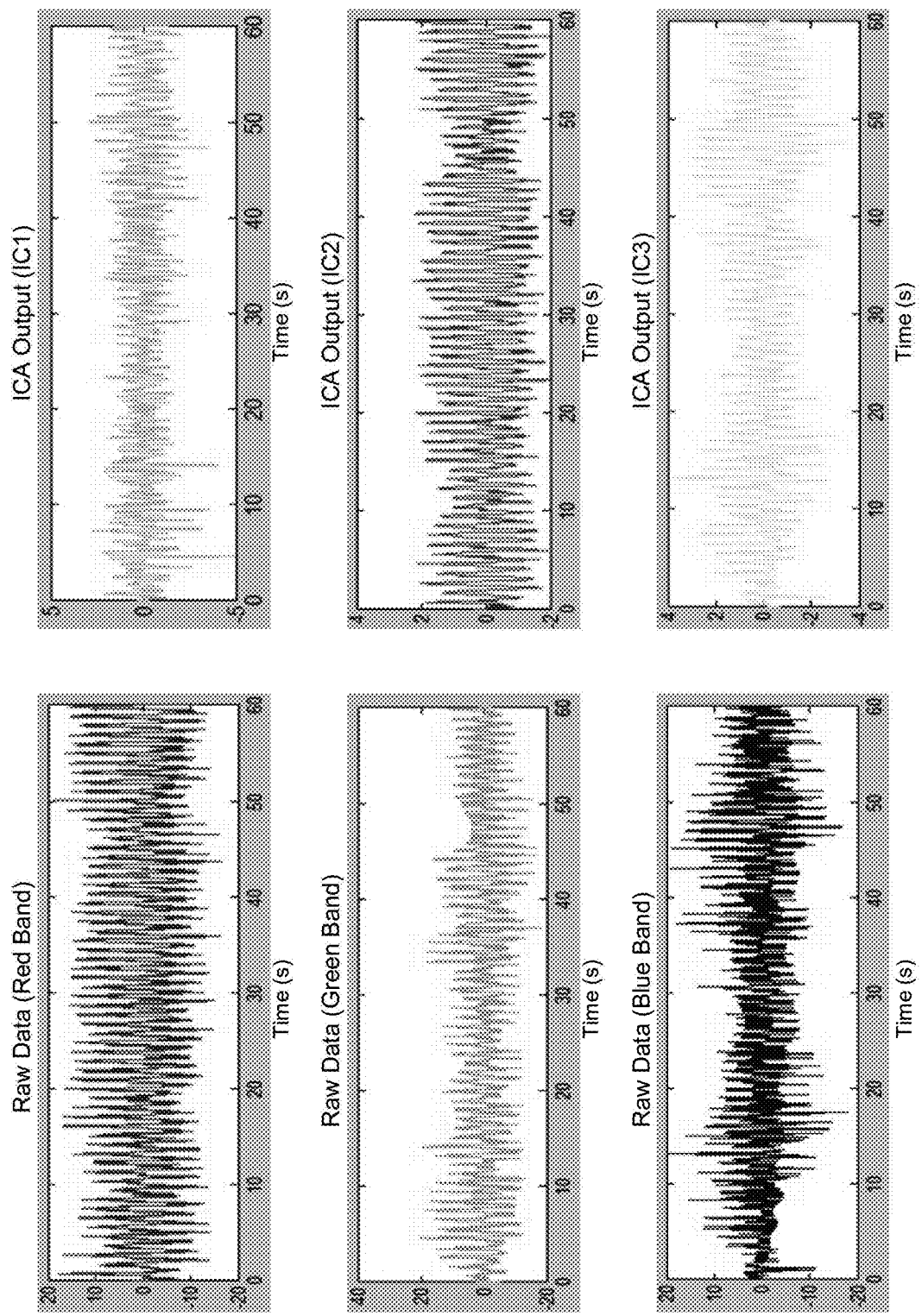
FIG. 6 shows an example of raw data from 3 bands (red, green, and blue) and the set of components that is output from an exemplary Independent Component Analysis (ICA) algorithm.

IC2 (Shown in FIG. 6) is the component that includes a pulse signal with the highest accuracy for cardiac pulse detection. Thus, IC2 is sent to Step S5.

Step S5 applies a bandpass filter with a filter size of 250 and pass band between 0.8 to 8 Hz to remove high frequency components for further denoising and the output signal is called the blood wave (BW) signal.

In Step S6, data processing device 30 uses a blind deconvolution (BDC) method to detect peaks from the observed BW signals. The BDC method uses the available BW signals and decomposes them into an input sequence ($\hat{x}[n]$), that is constrained to resemble an impulse train, and an estimated impulse response ($\hat{c}[n]$) of the cardiovascular system. These two parameters are initialized using the collected data. Based on the inventor's observations of the BW signals and the associated data, it is believed that the human body acts as a lowpass filter (LPF). Therefore, data processing device 30 initializes the human body response ($\hat{c}[n]$) to a heartbeat signal as a lowpass filter (p samples). To estimate an initial input signal ($\hat{x}[n]$), data processing device 30 applies a sinusoidal curve fitting algorithm to the BW signals and uses the detected peaks from each cycle to construct an impulse train (m samples). Then a Gaussian kernel with σ=0.1 is used as an initial estimate of the human body response ($\hat{c}[n]$).

The BDC algorithm uses the closed form of the linear least squares (LS) solution ($x=(S'S)^{-1}S'y$). The closed form of the LS is driven from the model $y=Sx+e$ and estimates the input signal ($\hat{x}$) by minimizing the error between the original BW signal (y) and the estimated signal ($\hat{y}$). In the equation, S is a convolution matrix with m+(p−1) rows and m columns. Row i of S contains the flipped and shifted (by i−1) copy of c, and therefore, the columns of S are identical but shifted, which results in a band matrix. Thus, there are two unknown parameters, the system response and the input to the system response. Using LS minimization, these two parameters are estimated iteratively, with an iteration control parameter (β=0.0005) to control the number of iterations, and a ridge penalty tuning parameter (α=0.0007) to prevent the singularity issues. At each iteration, the MSE between the original (y) and the estimated BW signal ($\hat{y}[k]$) is computed, and the algorithm converges when the MSE reaches a steady state value (e.g., |$MSE_{old}$−$MSE_{new}$|<0.001). Alternating between estimating $\hat{x}[k]$ and $\hat{S}[k]$ to determine an optimized estimate makes this algorithm a blind deconvolution algorithm. Both the input and the impulse response of the system are estimated in an iterative fashion, without the need of knowing one of them, as in a normal deconvolution problem. The detailed description of the algorithm is as follows:

1. Estimate $\hat{x}[k+1]$ using regularization. Since the columns of S are the shifted copies of the impulse response, they are strongly correlated, and therefore, introduce singularity issues, which leads to the ill-conditioned S matrix. Regularization helps with conditioning the matrix and mitigating singularity problems. Regularization is introduced through penalties such as the L0, L1, and L2 norms. Because the estimated ($\hat{x}[k+1]$) signal with sparse spikes represents an impulse train, the L0 penalty is used. The regularization parameter, W is a diagonal matrix and the penalties (L0, L0, and L2) can be represented using the equations below:

$$W_{jj}[k] = \left(\frac{1}{(\hat{x}_j[k])^2 + \beta^2}\right) \text{ (L0 penalty)}$$

$$W_{jj}[k] = \left(\frac{1}{\sqrt{(\hat{x}_j[k])^2 + \beta^2}}\right) \text{ (L1 penalty)}$$

$$W_{jj}[k] = 1 \text{ (L2 penalty)}$$

$$\hat{x}[k+1] = \left(\hat{S}[k]^T \hat{S}[k] + \alpha W[k]\right)^{-1} \hat{S}[k]^T y$$

Where, j represents the location in the $\hat{x}$ vector and jj the diagonal location in the W matrix.

2. Estimate $\hat{S}[k+1]$. Since the human body's system response function is not known, may vary from subject to subject, and may vary for a subject over the time, the system response to a given heartbeat signal is estimated iteratively using closed form solution of the LS minimization. Three steps involved to estimate $\hat{S}[k+1]$ are discussed below:

a. Estimate X[k], the convolution matrix. The rows of which are the shifted copies of the most recent input estimate $\hat{x}[k+1]$).

$$X[k] = \begin{bmatrix} \hat{x}[k+1, p+1-n] \\ \hat{x}[k+1, p+2-n] \\ \hat{x}[k+1, p+3-n] \\ \vdots \\ \hat{x}[k+1, p+i-n] \end{bmatrix}$$

b. Estimate $\hat{c}[k+1]$, the updated impulse response. To estimate this parameter, a regularization is not needed because this is a well-conditioned regression problem as the size of the convolution kernel ($\hat{c}$) is much smaller than the input ($\hat{x}$) and the output (y) signals.

$$\hat{c}[k+1] = (X[k]^T X[k])^{-1} X[k]^T y$$

c. Construct $\hat{S}[k+1]$, the updated convolution, matrix. The rows of $\hat{S}[k+1]$ are the flipped and shifted copies of the most recent impulse response estimate ($\hat{c}[k+1]$).

$$\hat{S}[k] = \begin{bmatrix} \hat{c}[k+1, p+1-n] \\ \hat{c}[k+1, p+2-n] \\ \hat{c}[k+1, p+3-n] \\ \vdots \\ \hat{c}[k+1, p+i-n] \end{bmatrix}$$

3. Estimate $\hat{y}[k+1]$, the estimated BW signal $$\hat{y}[k+1] = \hat{S}[k+1]\hat{x}[k+1]$$

4. Compute MSE between the original (y) and the estimated ($\hat{y}[k+1]$) BW signals $$MSE_{new}[k+1] = \|y - \hat{y}[k+1]\|^2$$

5. Test for the algorithm convergence $$\text{Convergence} = \begin{cases} \text{Yes} & , |MSE_{new}[k+1] - MSE_{old}| < \text{Tolerance} \\ \text{No} & , MSE_{old} = MSE_{new}[k+1] \end{cases}$$

6. If convergence is achieved, quit loop; otherwise, repeat from step 1.

Figure 10:
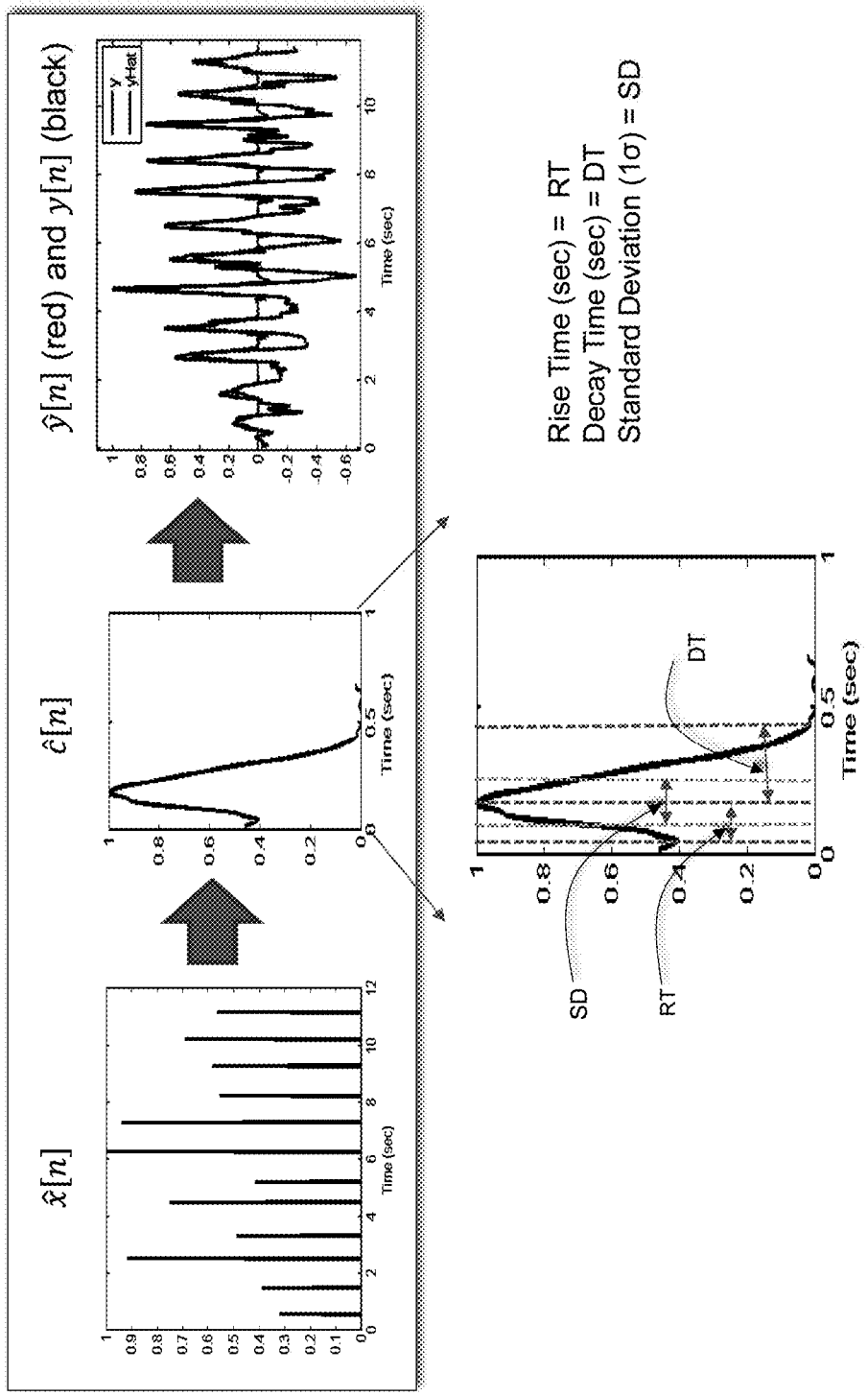
FIG. 10 shows blind deconvolution (BDC) estimated input signal ($\hat{x}$), actual output (y), estimated output ($\hat{y}$), estimated impulse response ($\hat{c}$), and characteristics of $\hat{c}$, which are rise time (RT), decay time (DT), and standard deviation (SD)

Following the BDC method, one output of step S6 is the subject-specific impulse response ($\hat{c}$ in FIG. 10) and its features. The impulse response features include:

RT—rise time of $\hat{c}$ (in FIG. 10) in seconds

DT—decay time of $\hat{c}$ (in FIG. 10) in seconds

SD—standard deviation (1σ) of $\hat{c}$ (in FIG. 10) in seconds

Some of the estimated impulse response features are used as inputs to step S10B, the data clustering block, which generates a data repository for identifying subjects (an example of data clustering method to generate data repository is discussed in paragraph hereafter).

Following the BDC method, another output of S6 is the set of R-peak locations (peaks in the BW signal, impulse locations in x̂ in FIG. 10), which are used to compute RR-intervals (the time differences between consecutive R-peaks). A series of these RR-intervals make the RR-interval signal that is then further processed to generate HRV features discussed hereafter.

Step S7 computes features based on the RR-interval signal. The two types of features are stress-specific HRV features and ID-specific HRV features. In one embodiment the six stress-specific HRV features are significantly different (p-value <0.05) under two physiological conditions and therefore are used to define subject-specific baseline for stress measurement. These features include:

a. HRVTi—HRV triangular index
   D(t)=density distribution of the histogram of RR-interval
   Y=maximum value of D(t)

Figure 4:
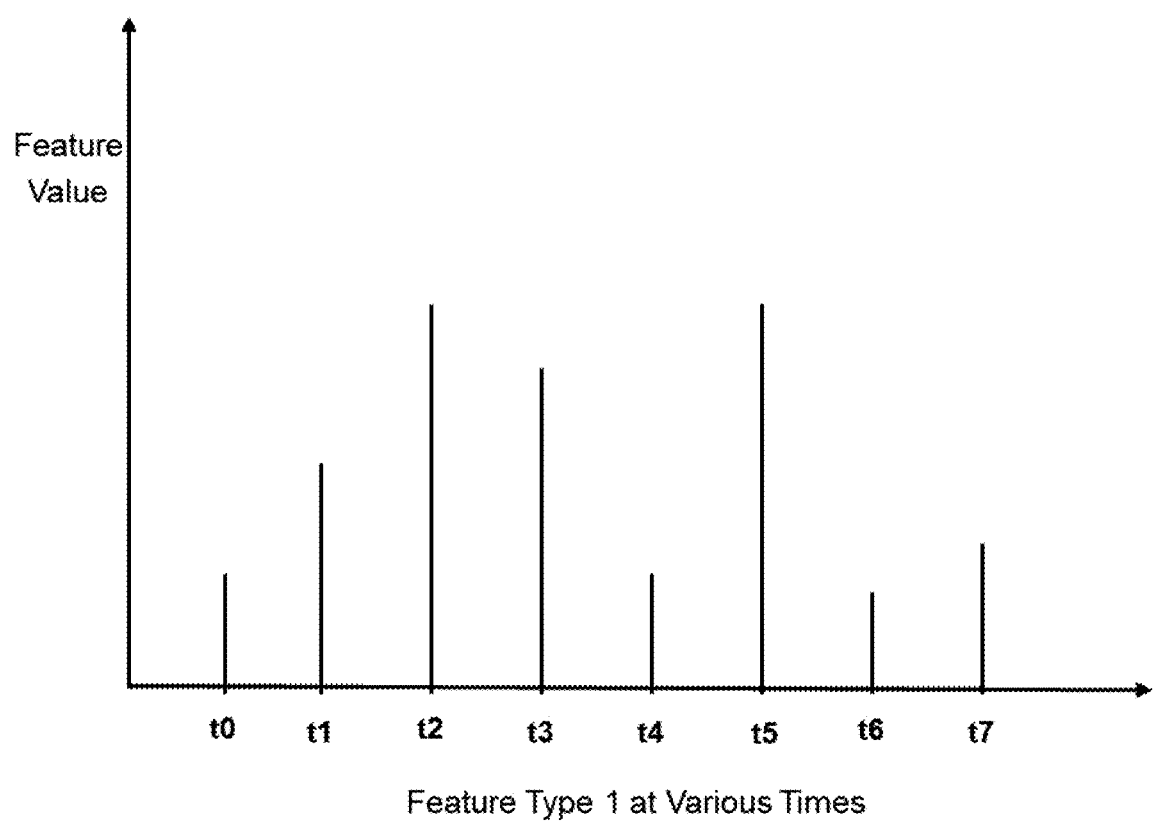
FIG. 4 shows data from an exemplary baseline data acquisition process.

$HRVTi=D(t)/Y$ b. pVLF (%)—Percentage of the sum of absolute very low frequency (0.003-0.05 Hz)
c. PeakHF (Hz)—Peak of the high frequency
d. pLF (%)—Percentage of the sum of absolute low frequency (0.01-0.15 Hz)
e. nHF (%)—High frequency normalized to total power high frequency
f. LFHF—The ration of LF to HF In another embodiment, step S7 computes seven ID-specific HRV features that are significantly different between subjects (p-value <0.05) and insensitive to change in physiological states (variance <0.01%). These features are used to generate a data repository, which is then compared against HRV features and impulse responses from individuals (in FIG. 9) to identify individuals. The list of ID-specific HRV features for identifying subjects include:

IBI (ms)—Time interval between successive heart beats
Min (ms)—Minimum IBI
Mean (ms)—Average IBI
Median (ms)—Median IBI
pNNx (ms)—Percentage of successive normal-to-normal (NN) heart beat interval (or IBI) that differ more than x ms
MeanHR (bpm)—Average heart rate
pHF (%)—Percentage of the sum of absolute high frequency Accordingly, the HRV analysis provides feature values that are collected over time. FIG. 4 shows an exemplary feature value (computed in Step S7) as it changes in value over time. From $t_0$ to $t_3$, there is significant variance, as shown in the variance plot. During this time, output device 40 shows a "red" indicator, or the raw variance or feature value data. As the variance in the feature values reaches a steady-state, output device 40 shows this raw data, or shows a "yellow" and then "green" indicator when the baseline is acquired (at least 5 samples). For each feature, the variance value at the steady-state is used as a predetermined threshold for that specific feature. This allows a user to know how long to wait before asking potentially stress inducing questions. Further, if the subject never completes the baseline data due to high variability in the computed feature values, this is an anomaly that may require further investigation. Thus, for example, when a law enforcement officer questions a subject after a car crash, the officer waits until the subject has recovered from the initial stress of the crash first.

Figure 5:
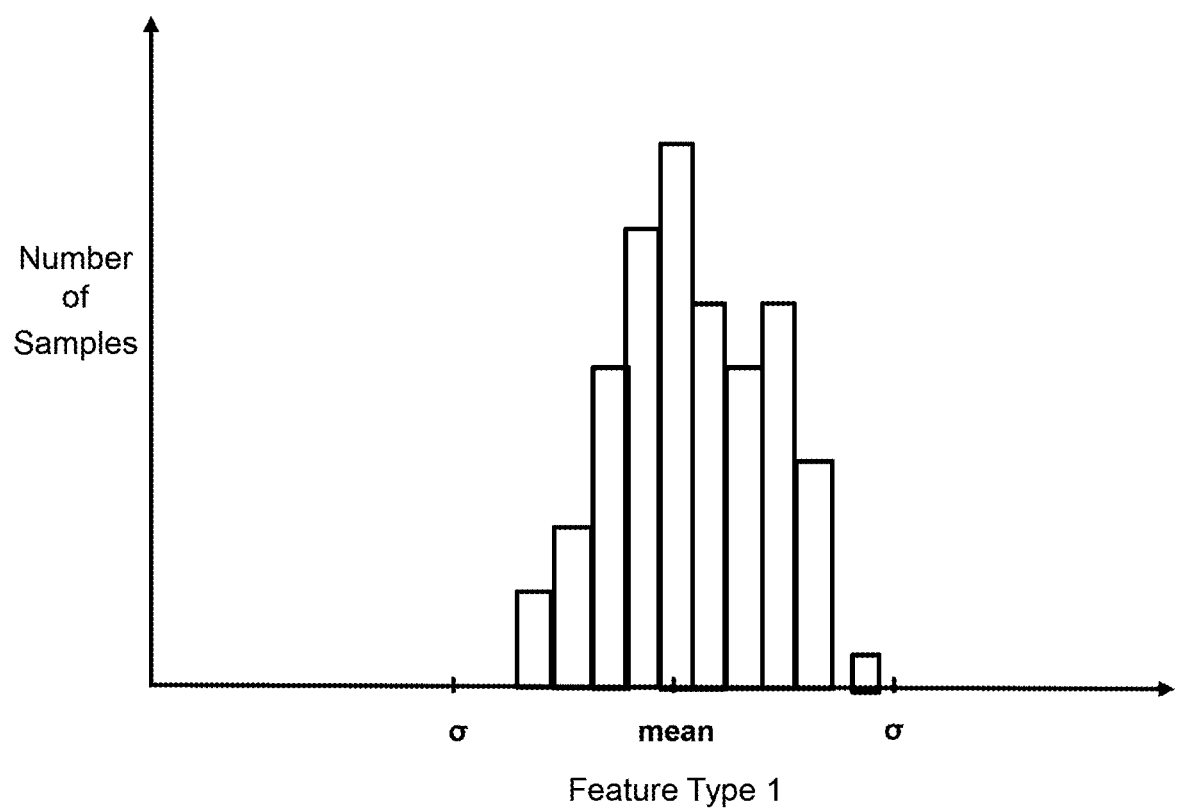
FIG. 5 shows an exemplary histogram of feature values.

FIG. 5 shows a histogram of feature value data from baseline data collection. If future data from the observed subject falls outside of the 1σ range, that alone could be an anomaly. Output device 40 shows the raw data in this case, or simply provides an audio or visual "anomaly alarm."

In this regard, potentially stress inducing events may be included in the baseline data collection time, such that the data collection time includes a baseline "not stressed" time and a potentially "stressed" time. In this regard, if a stress inducing event is included in the collection time for Step S11 and the subject is found to be "not stressed" in Step S20, output device 40 could indicate this anomaly. Not changing in stress level even during a stress inducing event may be due to the subject being under the influence of drugs, or the subject being under continual stress. For example, a customs official questioning a person attempting to smuggle illegal material into the country may feel high stress even before the official begins asking any questions. Output device 40 could indicate to the customs official anomalous behavior so that the subjects exhibiting these characteristics can be further screened.

Thus, feature values from multiple features are computed and sent to Step S10A.

In Step S8, forehead and palm data (spatial average of 121 signals within green band) from sensor 20 are passed through an infinite impulse response (IIR) bandpass filter. In one embodiment, this filter has a bandwidth range of 0.3-8 Hz.

Step S9 includes determining the peaks from the data output by the IIR filter. BW signals from two locations are used, such as the forehead and the palm of the subject. The dPTT value is calculated by identifying the peak position in the correlation function between the BW signals from the two locations, which is the time difference between the peaks in the two different locations. The present inventor found that this time difference is generally between about 5 and 30 ms.

However, two extra steps may be necessary before the correlation measurement can take place. The first is the definition of the ROIs for detecting BW signals, and the second is upsampling of detected BW signals to overcome a low frame rate limitation of sensor 20.

While averaging the intensity signal over larger areas is acceptable if the data is for the HRV analysis, this approach may lead to errors in the calculation of the dPTT values. The reason for the errors is the potential different arterial pathways in the adjacent areas. This error results in significant differences in the arrival time of the BW. One solution to this problem is to define smaller ROIs, for example, in both the palm and the forehead. Then BW signals are determined for each smaller ROI.

Figure 7B:
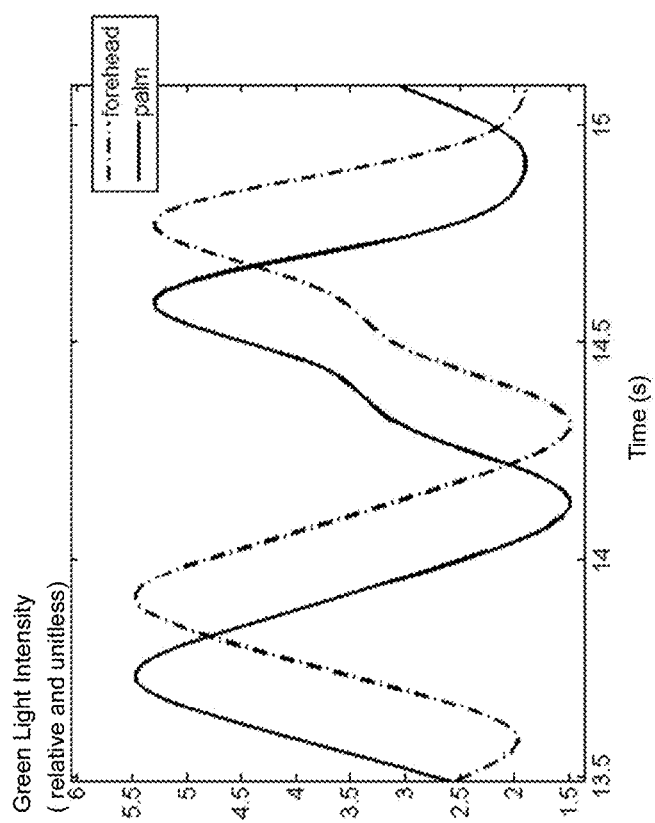
FIG. 7b shows a representative waveform and the time shift between the forehead and palm ROIs.
Figure 7A:
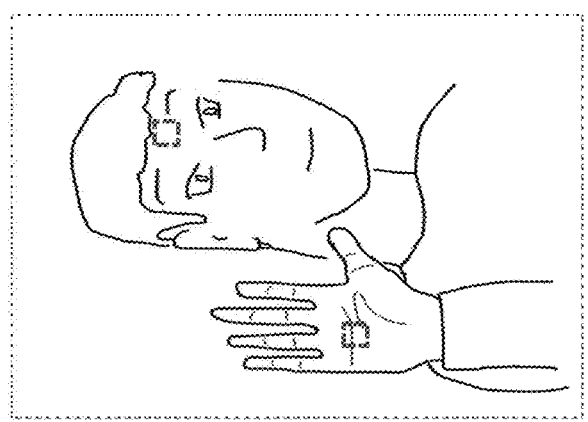
FIG. 7a shows forehead and palm Regions of Interest (ROIs)

The second possible change is to upsample the BW signals to overcome a low frame rate of sensor 20. In one embodiment, sensor 20 has a 59.9 frame per second frame rate, which is upsampled by a factor of 1000 for both ROIs. This allows a more precise estimation of the time difference between the two BW signals. A representative waveform and the time shift between the forehead and palm ROIs are shown in FIG. 7*b*.

Both of these modifications are within the scope of the invention as claimed.

The time differences computed in Step S9 are sent to Step S10A.

The baseline acquisition process computes weights for a data fusion equation and baseline fused features in Step S10A (the weights will be used in Step S20 of FIG. 8). Step S10A waits until the variance in the feature values drops below a predetermined threshold (discussed above with respect to Step S7). The weights are calculated using the following steps:

To generate the weights, one method is to use Least Mean Squares (LMS) method to estimate optimal weights for each HRV feature at each time index k.

$$X_k = \{x_{0k} x_{1k} \ldots x_{7k}\}$$

$$W_k = \{w_{0k} w_{1k} \ldots w_{7k}\}$$

$$Y_k = X_k^T W_k = W_k^T X_k$$

where columns of $X_k$ are the 7 features (HRV-1, HRV-2, . . . , HRV-6, dPTT) and k is a time index, $W_k$ are the weights associated with $X_k$, and $Y_k$ is the actual output value after fusion, and is referred as Fused Feature Value.

It is expected to have a high value of $Y_k$ under stress state. Therefore, the desired output value ($d_k$) is set to 1. The LMS algorithm is then used to estimate $W_k$ such that the error ($\varepsilon_k$) between $d_k$ and $Y_k$ is minimized.

$$\varepsilon_k = d_k - Y_k = d_k - X_k^T W_k = d_k - W_k^T X_k$$

Estimate optimal weights (W*) using the expected value operator E[x] to minimize the mean square error (MSE) of $\varepsilon_k$:

$$\varepsilon_k^2 = d_k^2 + W_k^T X_k X_k^T W_k - 2 d_k X_k^T W_k$$

$$E[\varepsilon_k^2] = E[d_k^2] + W_k^T E[X_k X_k^T] W_k - 2 E[d_k X_k^T] W_k$$

$$R = E[X_k X_k^T]$$

$$P = E[d_k X_k^T]$$

$$MSE \triangleq \xi = E[\varepsilon_k^2] = E[d_k^2] + W_k^T R W_k - 2 P^T W_k$$

$$\nabla = \frac{\partial \xi}{\partial w} = \left[ \frac{\partial \xi}{\partial w_{0k}} \frac{\partial \xi}{\partial w_{1k}} \ldots \frac{\partial \xi}{\partial w_{Lk}} \right]$$

$$\nabla = 2RW - 2P$$

Minimize gradient to determine optimal weights (W*)

$$\overline{\nabla} = 2RW - 2P = 0$$

$$2RW^* = 2P$$

$$W^* = R^{-1} P$$

The minimized MSE ($\xi_{min}$) is also be used to generate a performance surface:

$$\xi_{min} = E[\varepsilon_k^2] = E[d_k^2] + W_k^T R W_k - 2 P^T W_k$$

$$\xi_{min} = E[\varepsilon_k^2] = E[d_k^2] + [R^{-1} P]^T R [R^{-1} P] - 2 P^T [R^{-1} P]$$

Performance surface utilizes three rules:
1. Identity rule for any square matrix: $A^{-1} A = I$
2. Transpose of a matrix product: $[AB]^T = B^T A^T$
3. Symmetry of the input correlation matrix: $R^T = R$; $[R^{-1}]^T = R^{-1}$ $$\xi_{min} = E[\varepsilon_k^2] = E[d_k^2] + P^T R^{-1} R \, R^{-1} P - 2 P^T R^{-1} P$$

$$\xi_{min} = E[\varepsilon_k^2] = E[d_k^2] - P^T R^{-1} P$$

$$\xi_{min} = E[\varepsilon_k^2] = E[d_k^2] - P^T W^*$$

Thus, weights for each time index (k) are computed using the LMS method. However, alternate options to compute weights for each time index may be adapted such as Newton's method in multidimensional space, or Steepest Decent method. Once the weights are determined, a histogram of fused values (as shown in FIG. 5) is made using baseline data and the calculated weights. A standard deviation of the baseline ($1\sigma_b$) is also calculated using the fused values in the histogram.

The step S10B data clustering operation is performed to generate subject-specific clusters of subject-specific features (HRV features from step S7 and impulse response features (RT, DT, and SD) from step S6) using least discriminant analysis (LDA) method. To increase the confidence in correct match, the data are clustered such that the within-subject scatter is minimized and between-subject distance is maximized. FIG. 11a shows an example of two features from two subjects before projecting onto the LDA domain (left plot) and the two features from the two subjects after projecting them onto the LDA domain. Notice, there is a large overlap between the two clusters (blue and red stars in FIG. 11a, left plot), but this overlap is minimized when the features from the two subjects are projected onto an LDA domain (blue and red circles in FIG. 11b, right plot). FIG. 11b, right plot shows the centroids of the two clusters (blue and red squares), which are compared with the test subject (green square) by means of Euclidean distance to identify the best match. The output of the step S10B is the data repository in the LDA domain (the data repository will be used in Step S28 of FIG. 9).

The step S10A computes weights for a data fusion equation and baseline fused features (the output of this step will be used in Step S20 of FIG. 8). Step S10A waits until the variance in the feature values drops below a predetermined threshold (discussed above with respect to Step S7). The weights are calculated using the following steps:

Once the baseline acquisition process is finished, facial video recordings (inputs of FIG. 8) are taken to identify if the observed subject is under physiological stress state (output of FIG. 8). This process is shown in FIG. 8 and described hereinafter.

Steps S11-S19 are analogous to the corresponding Steps S1-S9. The main difference between the process shown in FIG. 3 and the process shown in FIG. 8 will be in Steps S20 and S20A.

In Step S11, data processing device 30 defines two ROIs of pixels within the video. In one example (e.g., FIG. 7a), one. ROI is an 11×11 pixel square area on the forehead and the other ROI is an 11×11 pixel square area on the palm. In this example, data processing device 30 constructs an 1×11×N matrix for each ROI (where N=number of frames). Within each ROI, 121 signals are generated from the RGB bands. The signals from forehead are processed using steps S11-S17 and HRV features are generated. The signals from Green band (acquired from both palm and forehead) are spatially averaged and processed using steps S18-S19, and dPTT feature is computed. Details of steps S11-S19 are discussed in the subsequent sections.

In Step S12, data processing device 30 removes baseline variations by applying a highpass filter to the raw individual pixel signals from the red, green, and blue bands. The highpass filter has a finite impulse response filter of order 250 and a frequency cutoff of 0.8 Hz. The filtered signals are then used as inputs to the Principal Component Analysis (PCA) algorithm, with the analysis running independently for each color channel.

In Step S13, data processing device 30 denoises (removes phase shift) RGB signal using PCA. One embodiment of an exemplary PCA algorithm is as follows. Data processing device 30 creates a matrix X with the columns representing signal recordings from each repeated collection of data. X can then be considered to have the form $X = USV^T$, where the columns of U contain the eigenvectors of $XX^T$, S is the diagonal matrix, and the rows of $V^T$ are the contributions of each eigenvector to each instance of the signal under examination. The present inventor discovered that the maximum variability in the data resides in the first eigenvector, and therefore this eigenvector is used to determine the PCA components with the best signal in the first component from RGB bands (noted hereinafter $\overrightarrow{asPC1_R}$, $\overrightarrow{PC1_G}$, $\overrightarrow{PC1_B}$). The present inventor further noted a heart-beat-like periodicity in the PC1 component in all three bands.

In Step S14, data processing device 30 selects a source from the PC1 component of the RGB data by applying an Independent Component Analysis (ICA) algorithm. The ICA algorithm is based on two principles: 1) Nonlinear decorrelation (whitening) and 2) maximum nongaussianity (rotation of whitened data). The ICA algorithm is applied to the PC1 components and the source signals (columns of S) are computed.

Basic equations to compute the source signals are listed below:

$$X=AS$$

Where, columns of matrix X are the PC1 components of the RGB data after applying the mixing matrix A to the matrix S.

The first step of the ICA algorithm is to compute estimated sources ($\hat{S}$) by first finding, the demixing matrix W that is proportional to the inverse of the mixing matrix A.

$$\hat{S}=WX$$

The whitening operation is performed on the input data X to remove any correlation between the signals. During this process, any correlation between the data is reduced to zero and similar variance for each data set. This operation generates the orthogonal basis for the reduced dimensionality components. To confirm the accuracy of the whitening operation, the computed covariance matrix of the whitened data is tested and confirmed if it is diagonal. Since W is approximately inversely proportional to the matrix A, it is used to rotate the whitened data to generate expected independent components.

IC2 (Shown in FIG. 6) is the component that includes a pulse signal with the highest accuracy for cardiac pulse detection. Thus, IC2 is sent to Step S15.

Step S15 applies a bandpass filter with a filter size of 250 and pass band between 0.8 to 8 Hz to remove high frequency components for further denoising and the output signal is called the blood wave (BW) signal.

In Step S16, data processing device 30 uses a blind deconvolution (BDC) method to detect peaks from the observed BW signals. The BDC method uses the available BW signals and decomposes them into an input sequence ($\hat{x}[n]$), that is constrained to resemble an impulse train, and an estimated impulse response ($\hat{c}[n]$) of the cardiovascular system. These two parameters are initialized using the collected data. Based on the inventor's observations of the BW signals and the associated data, it is believed that the human body acts as a lowpass filter (LPF). Therefore, data processing device 30 initializes the human body response ($\hat{c}[n]$) to a heartbeat signal as a lowpass filter (p samples). To estimate an initial input signal ($\hat{x}[n]$), data processing, device 30 applies a sinusoidal curve fitting algorithm to the BW signals and uses the detected peaks from each cycle to construct an impulse train (m samples). Then a Gaussian kernel with $\sigma=0.1$ is used as an initial estimate of the human body response ($\hat{c}[n]$).

The BDC algorithm uses the closed form of the linear least squares (LS) solution ($x=(S'S)^{-1}S'y$). The closed form of the LS is driven from the model $y=Sx+e$ and estimates the input signal ($\hat{x}$) by minimizing the error between the original BW signal (y) and the estimated signal ($\hat{y}$). In the equation, S is a convolution matrix with m+(p−1) rows and m columns. Row i of S contains the flipped and shifted (by i−1) copy of c, and therefore, the columns of S are identical but shifted, which results in a band matrix. Thus, there are two unknown parameters, the system response and the input to the system response. Using LS minimization, these two parameters are estimated iteratively, with an iteration control parameter ($\beta=0.0005$) to control the number of iterations, and a ridge penalty tuning parameter ($\alpha=0.0007$) to prevent the singularity issues. At each iteration, the MSE between the original (y)) and the estimated BW signal ($\hat{y}[k]$) is computed, and the algorithm converges when the MSE reaches a steady state value (e.g., $|MSE_{old}-MSE_{new}|<0.001$). Alternating between estimating $\hat{x}[k]$ and $\hat{S}[k]$ to determine an optimized estimate makes this algorithm a blind deconvolution algorithm. Both the input and the impulse response of the system are estimated in an iterative fashion, without the need of knowing one of them, as in a normal deconvolution problem. The detailed description of the (BDC) algorithm is as previously described, incorporated herein by reference.

Following the BDC method, the R-peaks (peaks in the BW signal) are determined from the BW signal, and then RR-intervals, which are the differences between consecutive R-peaks. A series of these RR-intervals make the RR-interval signal that is then further processed to generate HRV features discussed hereafter.

Step S17 computes features based on the RR-interval signal. In one embodiment, the following six stress-specific features that are significantly different (p-value <0.05) under two physiological conditions are computed for HIV analysis:

g. HRVTi—HRV triangular index
  D(t)=density distribution of the histogram of RR-interval
  Y=maximum value of D(t)

$$HRVTi=D(t)/Y$$

h. pVLF (%)—Percentage of the sum of absolute very low frequency (0.003-0.05 Hz)
i. PeakHF (Hz)—Peak of the high frequency
j. pLF (%)—Percentage of the sum of absolute low frequency (0.01-0.15 Hz)
k. nHF (%)—High frequency normalized to total power high frequency
l. LFHF—The ration of LF to HF Accordingly, the HRV analysis provides feature values that are collected over time.

In Step S18, forehead and palm data (spatial average of the signals within green band) from sensor 20 are passed through an infinite impulse response (IIR) bandpass filter. In one embodiment, this filter has a bandwidth range of 0.3-8 Hz.

Step S19 includes determining the peaks from the data output by the IIR filter. BW signals from two locations are used, such as the forehead and the palm of the subject. The dPTT value is calculated by identifying the peak position in the correlation function between the BW signals from the two locations, which is the time difference between the peaks in the two different locations. The present inventor found that this time difference is generally between about 5 and 30 ms.

As prior detailed for Step S9, however, two extra steps may be necessary before the correlation measurement can take place. That is, smaller regions of interest of pixels are defined within said video image and the blood wave signals are upsampled as needed before the correlation measurement can take place for Step S19. Those two extra steps are incorporated herein by reference from the prior detailed discussion.

In Step S20, the Baseline Feature Weights (generated in Step S10A) are used with feature values generated in Steps S17 and S19 to create a final Fused Feature Value ($Y_k$, the value after fusion).

Once the final Fused Feature Value is calculated, it is compared in Step 20A to with the Baseline Fused Features (generated in Step S10A using the baseline data generated in Step S7 and Step S9) to create the final "stressed" or "not stressed" conclusion. The threshold is the Baseline Fused Features deviation $1\sigma_b$, but for various applications, it can be a multiple of this value. For example, some applications may use $0.5\sigma_b$ as a threshold to detect small changes in stress, and other applications may use $2\sigma_b$ as a threshold to be less sensitive to small changes in stress.

Finally, output device 40 provides the result to a user. In one embodiment, output device 40 is a visual display, which simply provides text indicating "stressed" or "not stressed." In another embodiment, output device 40 also provides additional data, such as the values of the features calculated by the HRV processing, and/or the time differentials calculated in the dPPT processing for in depth analysis by a user. In a further embodiment, the "stressed" or "not stressed" result are displayed using color differences on a display, such as red for "stressed" and green for "not stressed." In this manner, multiple subjects in the field of view (FOV) of a camera may be evaluated at the same time.

Alternatively, output device 40 can be a speaker. For example, an audio indication can be provided, such as one beep for "not stressed" and two beeps for "stressed," or silence for "not stressed" and any audio signal for "stressed."

FIG. 9 shows the processing for a device 10 that identifies a subject (output of FIG. 9) based on the non-contact data (facial video as input of FIG. 9) collected by sensor 20. In this case, two types of features that are used are 1) human body's impulse response features and 2) HRV features that are significantly different between subjects and insensitive to change in physiological states. To compute the two types of features only one ROI location on the subject is needed. Further, the baselining process of FIG. 3 is done to generate repositories with HRV features for identification and impulse responses before taking data, in a similar manner as the first embodiment.

Steps S21 to S26 are analogous to Steps S1-S6. One necessary difference is that only one ROI over the forehead is used, as noted previously.

In Step S21, data processing device 30 defines an ROI over forehead within the facial video. In this embodiment, data processing device 30 constructs an 11×11×N matrix for each ROI (where N=number of frames). Within each ROI, 121 signals are generated from the RGB bands.

In Step S22, data processing device 30 removes baseline variations by applying a highpass filter to the raw individual pixel signals from the red, green, and blue bands. The highpass filter has a finite impulse response filter of order 250 and a frequency cutoff of 0.8 Hz. The filtered signals are then used as inputs to the Principal Component Analysis (PCA) algorithm, with the analysis running independently for each color channel.

In Step S23, data processing device 30 denoises (removes phase shift) RGB signal using PCA. One embodiment of an exemplary PCA algorithm is as follows. Data processing device 30 creates a matrix X with the columns representing signal recordings from each repeated collection of data. X can then be considered to have the form $X=USV^T$, where the columns of U contain the eigenvectors of $XX^T$, S is the diagonal matrix, and the rows of $V^T$ are the contributions of each eigenvector to each instance of the signal under examination. The present inventor discovered that the maximum variability in the data resides in the first eigenvector, and therefore this eigenvector is used to determine the PCA components with the best signal in the first component from RGB bands (noted hereinafter as $\overrightarrow{PC1_R}$, $\overrightarrow{PC1_G}$, $\overrightarrow{PC1_B}$). The present inventor further noted a heart-beat-like periodicity in the PC1 component in all three bands.

In Step S24, data processing device 30 selects a source from the PC1 component of the RGB data by applying an Independent Component Analysis (ICA) algorithm. The ICA algorithm is based on two principles: 1) Nonlinear decorrelation (whitening) and 2) maximum nongaussianity (rotation of whitened data). The ICA algorithm is applied to the PC1 components and the source signals (columns of S) are computed.

Basic equations to compute the source signals are listed below:

$$X=AS$$

Where, columns of matrix X are the PC1 components of the RGB data after applying the mixing matrix A to the matrix S.

The first step of the ICA algorithm is to compute estimated sources ($\hat{S}$) by first finding the demixing matrix W that is proportional to the inverse of the mixing matrix A.

$$\hat{S}=WX$$

The whitening operation is performed on the input data X to remove any correlation between the signals. During this process, any correlation between the data is reduced to zero and similar variance for each data set. This operation generates the orthogonal basis for the reduced dimensionality components. To confirm the accuracy of the whitening operation, the computed covariance matrix of the whitened data is tested and confirmed if it is diagonal. Since W is approximately inversely proportional to the matrix A, it is used to rotate the whitened data to generate expected independent components.

IC2 (Shown in FIG. 6) is the component that includes a pulse signal with the highest accuracy for cardiac pulse detection. Thus, IC2 is sent to Step S25.

Step S25 applies a bandpass filter with a filter size of 250 and pass band between 0.8 to 8 Hz to remove high frequency components for further denoising and the output signal is called the blood wave (BW) signal.

In Step S26, data processing device 30 uses a blind deconvolution (BDC) method to detect peaks from the observed BW signals. The BDC method uses the available BW signals and decomposes them into an input sequence ($\hat{x}[n]$), that is constrained to resemble an impulse train, and an estimated impulse response ($\hat{c}[n]$) of the cardiovascular system. These two parameters are initialized using the collected data. Based on the inventor's observations of the BW signals and the associated data, it is believed that the human body acts as a lowpass filter (LPF). Therefore, data processing device 30 initializes the human body response ($\hat{c}[n]$) to a heartbeat signal as a lowpass filter (p samples). To estimate an initial input signal ($\hat{x}[n]$), data processing device 30 applies a sinusoidal curve fitting algorithm to the BW signals and uses the detected peaks from each cycle to construct an impulse train (m samples). Then a Gaussian kernel with σ=0.1 is used as an initial estimate of the human body response (ĉ[n]).

The BDC algorithm uses the closed form of the linear least squares (LS) solution $(x=(S'S)^{-1}S'y)$. The closed form of the LS is driven from the model y=Sx+e and estimates the input signal (x̂) by minimizing the error between the original BW signal (y) and the estimated signal (ŷ). In the equation, S is a convolution matrix with m+(p−1) rows and in columns. Row i of S contains the flipped and shifted (by i−1) copy of c, and therefore, the columns of S are identical but shifted, which results in a band matrix. Thus, there are two unknown parameters, the system response and the input to the system response. Using LS minimization, these two parameters are estimated iteratively, with an iteration control parameter (β=0.0005) to control the number of iterations, and a ridge penalty tuning parameter (α=0.0007) to prevent the singularity issues. At each iteration, the MSE between the original (y)) and the estimated BW signal (ŷ[k]) is computed, and the algorithm converges when the MSE reaches a steady state value (e.g., $|MSE_{old}-MSE_{new}|<0.001$). Alternating between estimating x̂[k] and Ŝ[k] to determine an optimized estimate makes this algorithm a blind deconvolution algorithm. Both the input and the impulse response of the system are estimated in an iterative fashion, without the need of knowing one of them, as in a normal deconvolution problem. The detailed description of the (BDC) algorithm is as previously described, incorporated herein by reference.

Following the BDC method, subject-specific impulse response (ĉ) is estimated and features are calculated such as maximum amplitude, rise time, decay time, and standard deviation (1σ and 2σ). These impulse response features are then used as inputs to the step S28 compared with the impulse response repository (developed using output of S8 in FIG. 3).

Following the BDC method, the R-peaks (peaks in the BW signal) are determined from the BW signal, and then RR-intervals, which are the differences between consecutive R-peaks. A series of these RR-intervals make the RR-interval signal that is then further processed to generate ID-specific HRV features discussed hereafter.

In Step S27, the following features are calculated:
IBI (ms)—Time interval between successive heart beats
Min (ms)—Minimum IBI
Mean (ms)—Average IBI
Median (ms)—Median IBI
pNNx (ms)—Percentage of successive normal-to-non (NN) heart beat interval (or IBI) that differ more than x ms
MeanHR (bpm)—Average heart rate
pHF (%)—Percentage of the sum of absolute high frequency Step S28 is used to identify a subject profile. The subject profile includes ID-specific HRV features (output of Step S27) and impulse response features (output of Step S26), which are mapped onto the LDA generated data repository (generated in Step S10B). The subject profile is then compared against each cluster in the repository and scored by means of minimum Euclidian distance. FIG. 11b, right plot shows an example with centroids of the two clusters (blue and red squares), which are compared with the test subject (green square) by means of Euclidean distance (normalized range between 0 and 1), which is referred as score. The scores are then rank ordered in ascending order representing the best match with the smallest Euclidian distance and the least match with the largest Euclidian distance. If the Euclidian distance from S28 matches only a single known profile within a tolerance level (e.g., 0.2), that known profile is identified as the subject being monitored. In another embodiment, Step S28 may be used to determine all of the known profiles that match the calculated features (ID-specific HRV features and impulse response features) within the 0.2 tolerance level. All of the "close" known profiles could then be identified to a user of the device 10 through output device 40. Thus, this embodiment would need to store a database repository of known profiles, which are pre-measured ID-specific HRV features and impulse response features (such as listed in Step S26 and S27) for each of a plurality of people who may be the subject profile being analyzed.

Alternatively, output device 40 can be a display screen that displays all of the pre-stored profiles that are "close" to the currently measured subject profile. If no known profile is "close," output device 40 also provides such information. Output device 40 also has an audio output device that provides an audible sound when the currently measured subject profile is identified as possibly matching a list of particular profiles, such as wanted criminals.

Thus, alternative implementations of the present invention can include: Hand held devices such as smart glasses, cellphones, and PCs/laptops/tablets. For example, smart glasses may provide the wearer a visual or audio indication that a person being spoken to is under stress. Thus, law enforcement could use such a device to interrogate suspects and get instant feedback as to whether or not the suspect increases in stress as a result of particular questions being asked. This could also be done with a cellphone.

In addition, this invention could be incorporated into a law enforcement shoulder camera. The camera could be configured to constantly determine stress of any subjects in view. If a subject's stress level increases, and audible warning can be provided to the officer to warn them the subject may react due to high stress. Further, anomalous readings (as described above) may indicate that the subject is under the influence of drugs or alcohol, and a same or different audible warning can be provided in such a case.

A doctor could also use such a device to get stress level feedback from patients as a result of questions asked by the doctor. In this case, the doctor may use a PC/laptop/tablet so as to view the raw data as well as the overall stress indication. This may help doctors treating patients reluctant to discuss any medical issues they are having, including those suffering from post-traumatic stress disorder (PTSD). In this case, the device stores data from multiple sessions with a patient. The data can be combined to provide overall stress trends for the subject. That is, the patients stress level at the start of each session may be measured during baseline acquisition. These baselines can be compared to determine if treatment is helping reduce the patient's stress. The weights calculated each time will also reflect either a trend in the patient's stress level, or random noise around a mean if the patient's stress is steady.

Larger systems may also be constructed incorporating the invention. For example, a system inside a vehicle may monitor a driver's stress level to determine whether or not the driver is paying attention to the road, or if the driver is under the influence of alcohol or drugs. In this case, the system would need a stress event creator, such as a display visible to the driver or an audible warning/stimulus. Stressful images may be occasionally shown to the driver using such a display or warnings could be provided audibly. If the driver's stress level is too low or too high in response (for example, determined by feature values being more than 1σ from the mean as shown in FIG. 5), the driver may not be paying attention, or may be under the influence of alcohol or drugs. Such a device could determine if the driver should not be driving due to impairment without the need for a chemical test such as a breathalyzer.

Another system incorporating the present invention is a system for studying a person with attention deficit hyperactivity disorder (ADHD). This system would include a video camera to measure stress level of the person and another video camera to detect the stressor (what the person is seeing). The system could then determine the person's stress level, and based on the video collected, identify the stimuli that triggers the person's ADHD.

As previously noted, a larger system could be used as border security, such as at an airport. Customs officials could receive a stress indication for the system based on questions the official asks an individual, while the raw data may be provided to additional customs officials in a closed room. Thus, both the raw data and the stress determination can be used to determine if further screening of an individual is necessary.

Systems in accordance with the present invention could also monitor the stress in individuals in a large crowd of people. For example, cameras could monitor the stress reaction simultaneously from individuals in a crowd of people waiting at an airport. A stress event could be created with a loudspeaker, for example announcing "Everyone carrying a weapon please see a security official." The system could determine which people in the crowd had their stress level rise as a result of the announcement, which could be an indication that they are carrying a concealed weapon.

Finally, a system for identifying persons could include the BW signatures of wanted criminals, and then the system could collect data on people in a public space, such as an airport or train station. In this way, law enforcement could passively search for wanted criminals at multiple locations at once.

The present written description uses examples to disclose the present subject matter, including the best mode, and also to enable any person skilled in the art to practice the present subject matter, including making and using any devices or systems and performing any incorporated and/or associated methods. While the present subject matter has been described in detail with respect to specific embodiments thereof, it will be appreciated that those, skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A baseline and repository acquisition data processing method for a sensor system comprising:
    a sensor directed towards a human subject under a daylight condition to capture video images of human skin, and output video signals,
    a data processing unit configured to determine multiple heart rate metrics of the human subject by data processing identified regions of interest of pixels of said video signals and derive a physiological characteristic of the human subject, and
    an output device configured to indicate said physiological characteristic of the human subject;
    the baseline and repository acquisition data processing method comprising the steps of:
        receiving RGB video signals by said data processing unit as individual RGB pixel signals collected for red, green and blue bands, from said sensor directed towards a human subject to establish baseline acquisition data;
        defining two regions of interest of pixels within a video image of said received RGB video signals, one region of interest being a forehead pixel area, and another region of interest being palm pixel area;
        removing baseline variations by applying a highpass filter to the individual RGB video signals for the red, green, and blue bands of the forehead pixel area, resulting in RGB pixel signals;
        denoise by removing phase shift from the RGB pixel signals using a principal component analysis algorithm, resulting in denoised RGB pixel signals;
        selecting a source from a PC1 component of the denoised RGB pixel data by applying an independent component analysis algorithm;
        applying a bandpass filter to remove high frequency components and further denoise RGB pixel signals, resulting in blood wave signals;
        using a blind deconvolution method to detect peaks from the blood wave signals and output subject-specific impulse response features as impulse response features;
        computing stress-specific HRV features and ID-specific HRV features based on measurements of interval between subsequent heartbeats, or RR-interval signals, to produce multiple feature values;
        passing forehead and palm data from said sensor through an infinite impulse response bandpass filter to output IIR filtered data;
        determining peaks from the IIR filtered data to estimate time differences between blood wave signals of the forehead data and the palm data;
        clustering said ID-specific HRV features said impulse response features to generate subject-specific clusters of subject-specific features using a least discriminant analysis method to result in a data repository in an LDA domain; and
        computing baseline feature weights for a data fusion equation and baseline fused features based on said multiple feature values of stress-specific HRV features and said time differences between blood wave signals of the forehead data and the palm data for output.

2. The baseline and repository acquisition data processing method recited in claim 1, wherein baseline acquisition data is taken over a significant period of time of about 30 seconds over multiple collections.

3. The baseline and repository acquisition data processing method recited in claim 1, wherein said applying of a bandpass filter to result in a blood wave signal uses a filter size of 250 and pass band between 0.8 to 8 Hz to remove high frequency components.

4. The baseline and repository acquisition data processing method recited in claim 1, wherein said infinite impulse response bandpass filter has a bandwidth range of 0.3-8 Hz.

5. The baseline and repository acquisition data processing method recited in claim 1, wherein smaller regions of interest of pixels are defined within said video image and/or the blood wave signals are upsampled as needed to determine peaks from the IIR filtered data to estimate time differences between blood wave signals of the forehead data and the palm data.

6. A stress detection data processing method using the baseline feature weights and the baseline fused features computed from the baseline and repository acquisition data processing method recited in claim 1, the stress detection data processing method comprising the steps of:

receiving new RGB video signals by said data processing unit as new RGB pixel signals collected for red, green and blue bands, from said sensor directed towards an human subject to identify if the human subject is under physiological stress state;

defining two regions of interest of pixels within a video image of said new RGB video signals, one region of interest being a forehead pixel area, and another region of interest being palm pixel area of the human subject;

removing baseline variations by applying a highpass filter to the individual RGB video signals for the red, green, and blue bands of the forehead pixel area, resulting in RGB pixel signals;

denoise by removing phase shift from the RGB pixel signals using a principal component analysis algorithm, resulting in denoised RGB pixel signals;

selecting a source from a PC1 component of the denoised RGB pixel data by applying an independent component analysis algorithm;

applying a bandpass filter to remove high frequency components and further denoise RGB pixel signals, resulting in blood wave signals;

using a blind deconvolution method to detect peaks from the blood wave signals;

computing stress-specific features based on measurements of interval between subsequent heartbeats, or RR-interval signals, to produce multiple feature values;

passing forehead and palm data from said sensor through an infinite impulse response bandpass filter to output IIR filtered data;

determining peaks from the BR filtered data to estimate time differences between blood wave signals of the forehead and the palm data;

using the baseline feature weights computed from the baseline and repository acquisition data processing method with said multiple feature values and said time differences between blood wave signals of the forehead data and the palm data to yield a final fused feature value; and comparing said final fused feature value to baseline fused features computed from the baseline and repository acquisition data processing method to identify if the human subject is under physiological stress state as an indication of a physiological characteristic of the human subject.

7. The stress detection data processing method recited in claim 6, wherein 30 seconds of visible video data is collected by the sensor, resulting in said new RGB video signals.

8. The stress detection data processing method recited in claim 6, wherein said applying of a bandpass filter to result in a blood wave signal uses a filter size of 250 and pass band between 0.8 to 8 Hz to remove high frequency components.

9. The stress detection data processing method recited in claim 6, wherein said infinite impulse response bandpass filter has a bandwidth range of 0.3-8 Hz.

10. The stress detection data processing method recited in claim 6, wherein smaller regions of interest of pixels are defined within said video image and/or the blood wave signals are upsampled as needed to determine peaks from the IIR filtered data to estimate time differences between blood wave signals of the forehead data and the palm data.

11. An individual identification method using the subject-specific clusters of subject-specific features from the baseline and repository acquisition data processing method recited in claim 1, individual identification method comprising the steps of:

receiving new RGB video signals by said data processing unit as new RGB pixel signals collected for red, green and blue bands, from said sensor directed towards an human subject's face to identify the human subject;

defining a forehead region of interest of pixels within a face image of said new RGB video signals;

removing baseline variations by applying a highpass filter to the individual RGB pixel signals for the red, green, and blue bands, resulting in RGB pixel signals;

denoise by removing phase shift from the RGB pixel signals using a principal component analysis algorithm, resulting in denoised RGB pixel signals;

selecting a source from a PC1 component of the denoised RGB pixel data by applying an independent component analysis algorithm;

applying a bandpass filter to remove high frequency components and further denoise RGB pixel signals, resulting in blood wave signals;

using a blind deconvolution method to detect peaks from the blood wave signals and estimate impulse response of the cardiovascular system;

computing features based on measurements of interval between subsequent heartbeats, or RR-interval signals, to calculate feature values of ID-specific HRV features;

using a subject profile of said feature values of ID-specific HRV features and the estimated impulse response of the cardiovascular system to compare the subject profile against each cluster of subject-specific features in the data repository of claim 6 until a known profile is best matched as the human subject being monitored.

12. The individual identification method recited in claim 11, wherein said subject profile is identified if a Euclidian distance of the comparison matches a known profile within a tolerance level of 0.2, said known profile being identified as the human subject being monitored.

13. The individual identification method recited in claim 11, wherein all known profiles that match the calculated features and estimated impulse response within a 0.2 tolerance level are identified for output to the output device.

14. The individual identification method recited in claim 11, wherein said ID-specific HRV features are:

time interval between successive heart beats;
minimum time interval between successive heart beats;
average time interval between successive heart beats;
median time interval between successive heart beats;
percentage of successive normal-to-normal heart beat interval that differ more than a threshold interval;
average heart rate; and
percentage of the sum of absolute high frequency.

15. The individual identification method recited in claim 14, wherein said data repository stores known profiles for retrieval, which known profiles contain said cluster of subject-specific features that are premeasured, estimated impulse response of the cardiovascular system, and weights for each individual who may be the human subject whose profile is being analyzed.

* * * * *